United States Patent
Dekker et al.

(10) Patent No.: US 10,239,093 B2
(45) Date of Patent: Mar. 26, 2019

(54) ULTRASOUND TRANSDUCER ASSEMBLY AND METHOD FOR MANUFACTURING AN ULTRASOUND TRANSDUCER ASSEMBLY

(71) Applicant: KONINKLIJKE PHILIPS N.V., Eindhoven (NL)

(72) Inventors: Ronald Dekker, Valkenswaard (NL); Vincent Adrianus Henneken, Utrecht (NL); Marcus Cornelis Louwerse, Nijmegen (NL); Maria Filomena Raganato, Veldhoven (NL)

(73) Assignee: Koninklijke Philips N.V., Endhoven (NL)

( * ) Notice: Subject to any disclaimer, the term of this patent is extended or adjusted under 35 U.S.C. 154(b) by 285 days.

(21) Appl. No.: 15/117,848

(22) PCT Filed: Mar. 2, 2015

(86) PCT No.: PCT/EP2015/054301
§ 371 (c)(1),
(2) Date: Aug. 10, 2016

(87) PCT Pub. No.: WO2015/135784
PCT Pub. Date: Sep. 17, 2015

(65) Prior Publication Data
US 2017/0008030 A1    Jan. 12, 2017

(30) Foreign Application Priority Data
Mar. 12, 2014    (EP) .................................... 14159036

(51) Int. Cl.
*B06B 1/02*    (2006.01)
*A61B 8/12*    (2006.01)
(Continued)

(52) U.S. Cl.
CPC .............. *B06B 1/0292* (2013.01); *A61B 8/12* (2013.01); *A61B 8/445* (2013.01); *A61B 8/4494* (2013.01);
(Continued)

(58) Field of Classification Search
CPC ......... B06B 1/0292; A61B 8/12; A61B 8/445; A61B 8/4494; G01N 29/2406; G01N 2291/101
See application file for complete search history.

(56) References Cited

U.S. PATENT DOCUMENTS 5,258,318 A    11/1993    Buti et al.
5,264,395 A    11/1993    Bindal et al.
(Continued)

FOREIGN PATENT DOCUMENTS

CN    1010868185 A        10/2010
CN    106413921 A    *    2/2017    ........... B06B 1/0292
(Continued)

OTHER PUBLICATIONS

Mimoun et al, "Flex-To-Rigid (F2R): A Novel Ultra-Flexible Technology for Smart Invasive Medical Instruments," Stretchable Electronics and Conformal Biointerfaces, Mater. Res. Soc. Symp. Proc. vol. 1271E, 2010, 6 Pages.
(Continued)

*Primary Examiner* — Daniel Pihulic

(57) ABSTRACT

The present invention relates to an ultrasound transducer assembly (10), in particular for intravascular ultrasound systems. The ultrasound transducer assembly comprises at least one silicon substrate element (30) including an ultrasound transducer element (14) for emitting and receiving ultrasound waves and including electrical connectors for electrically connecting the transducer element. The substrate element has a top surface (44), a bottom surface (46) and a
(Continued)

side surface connecting the top surface and the bottom surface. An isolation layer (32, 50) forms the side surface for electrically isolating the substrate element.

17 Claims, 18 Drawing Sheets

(51) Int. Cl.
*A61B 8/00* (2006.01)
*G01N 29/24* (2006.01)

(52) U.S. Cl.
CPC ... *G01N 29/2406* (2013.01); *G01N 2291/101* (2013.01)

(56) References Cited

U.S. PATENT DOCUMENTS

| | | | |
|---|---|---|---|
| 6,521,510 B1 | 2/2003 | Fisher et al. | |
| 2003/0161069 A1 | 8/2003 | Hipwell, Jr. et al. | |
| 2005/0146247 A1 | 7/2005 | Fisher et al. | |
| 2007/0128758 A1 | 6/2007 | Tanaka et al. | |
| 2007/0167814 A1* | 7/2007 | Wakabayashi | A61B 8/12 600/459 |
| 2008/0027320 A1* | 1/2008 | Bolorforosh | A61B 8/12 600/439 |
| 2009/0122651 A1* | 5/2009 | Kupnik | B06B 1/0292 367/181 |
| 2010/0262014 A1 | 10/2010 | Huang | |
| 2012/0091543 A1* | 4/2012 | Torashima | B06B 1/0292 257/415 |
| 2014/0038410 A1* | 2/2014 | Kraft | H01L 21/76898 438/637 |
| 2017/0008030 A1* | 1/2017 | Dekker | B06B 1/0292 |

FOREIGN PATENT DOCUMENTS

| | | | |
|---|---|---|---|
| EP | 1762182 A1 | 3/2007 | |
| EP | 2441530 A2 | 4/2012 | |
| EP | 2693456 A1 | 5/2014 | |
| EP | 2693467 A1 | 5/2014 | |
| EP | 3116662 A2 * | 1/2017 | B06B 1/0292 |
| WO | WO-2015135784 A3 * | 11/2015 | B06B 1/0292 |

OTHER PUBLICATIONS

Merzsch, et al., "Silicon Based Sensors and Functional Components Fabricated by ICP-RIE Cryogenic Dry Etching".
Memmi, et al., "Fabrication of capacitive micromechanical ultrasonic transducers by low-temperature process", Sensors and Actuators A 99, 2002, pp. 85-91.
Mescheder, "Modern Silicon-Based MEMS Technology", Smart Sensors and MEMS, pp. 255-272.
Ashruf, et al., "Electrochemical etch stop engineering for bulk micromachining", Mechatronics 8 (1998), pp. 595-612.
Zhuang, et al., "Interconnection and Packaging for 2D Capacitive Micromachined Ultrasonic Transducer Arrays Based on Through-Wafer Trench Isolation", MEMS 2006, Instanbul, Turkey, Jan. 22-26, 2006, pp. 270-273.

* cited by examiner

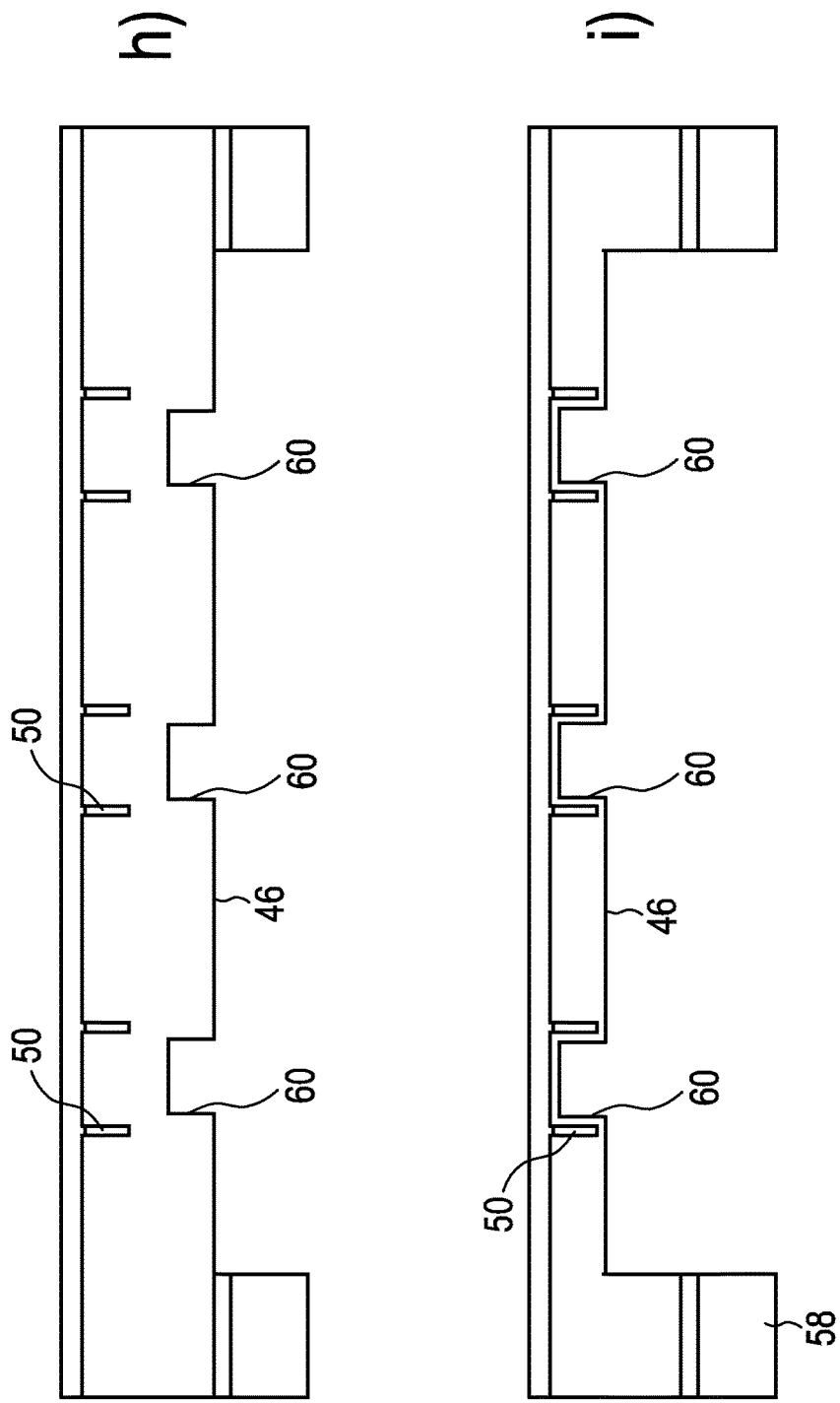

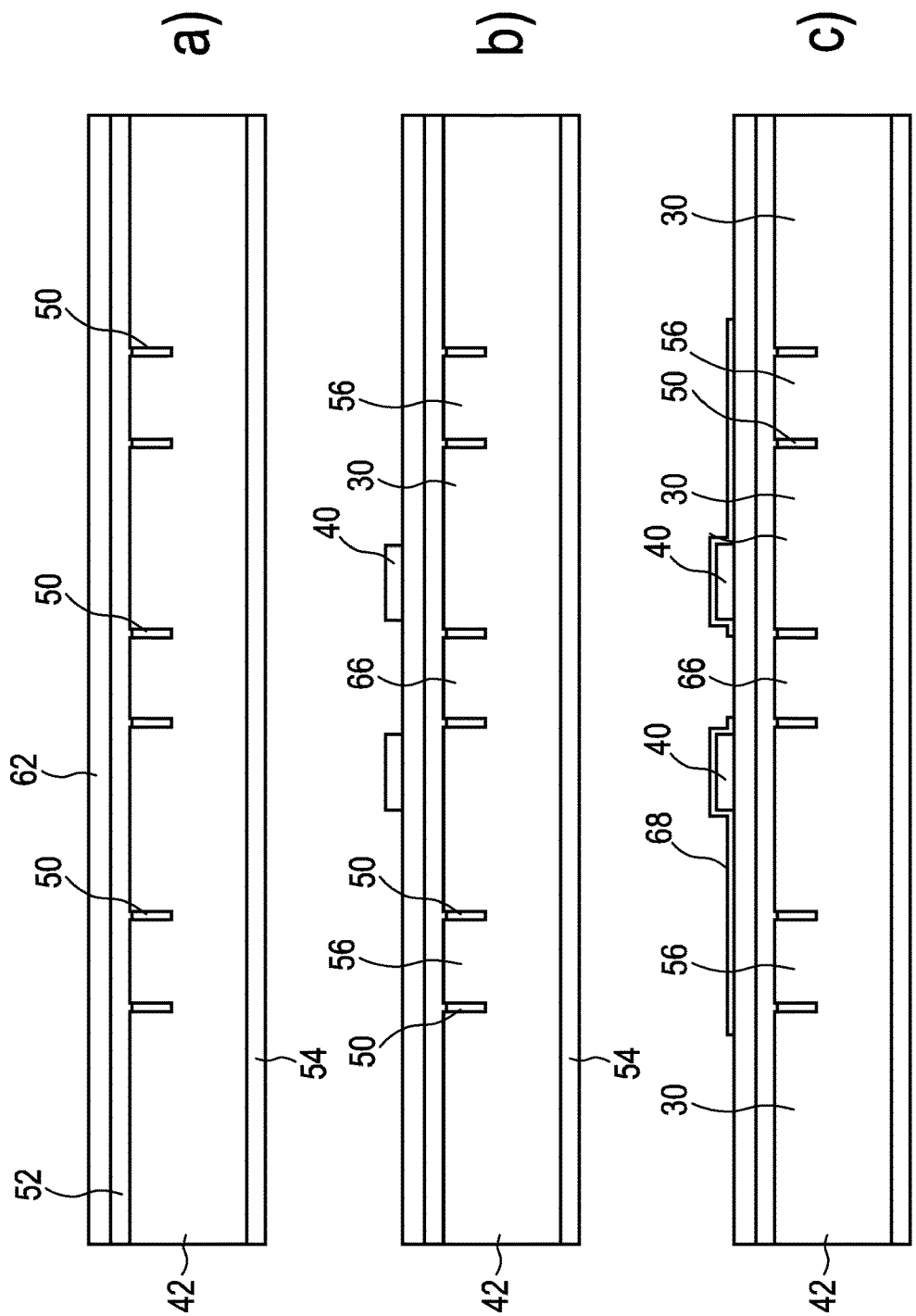

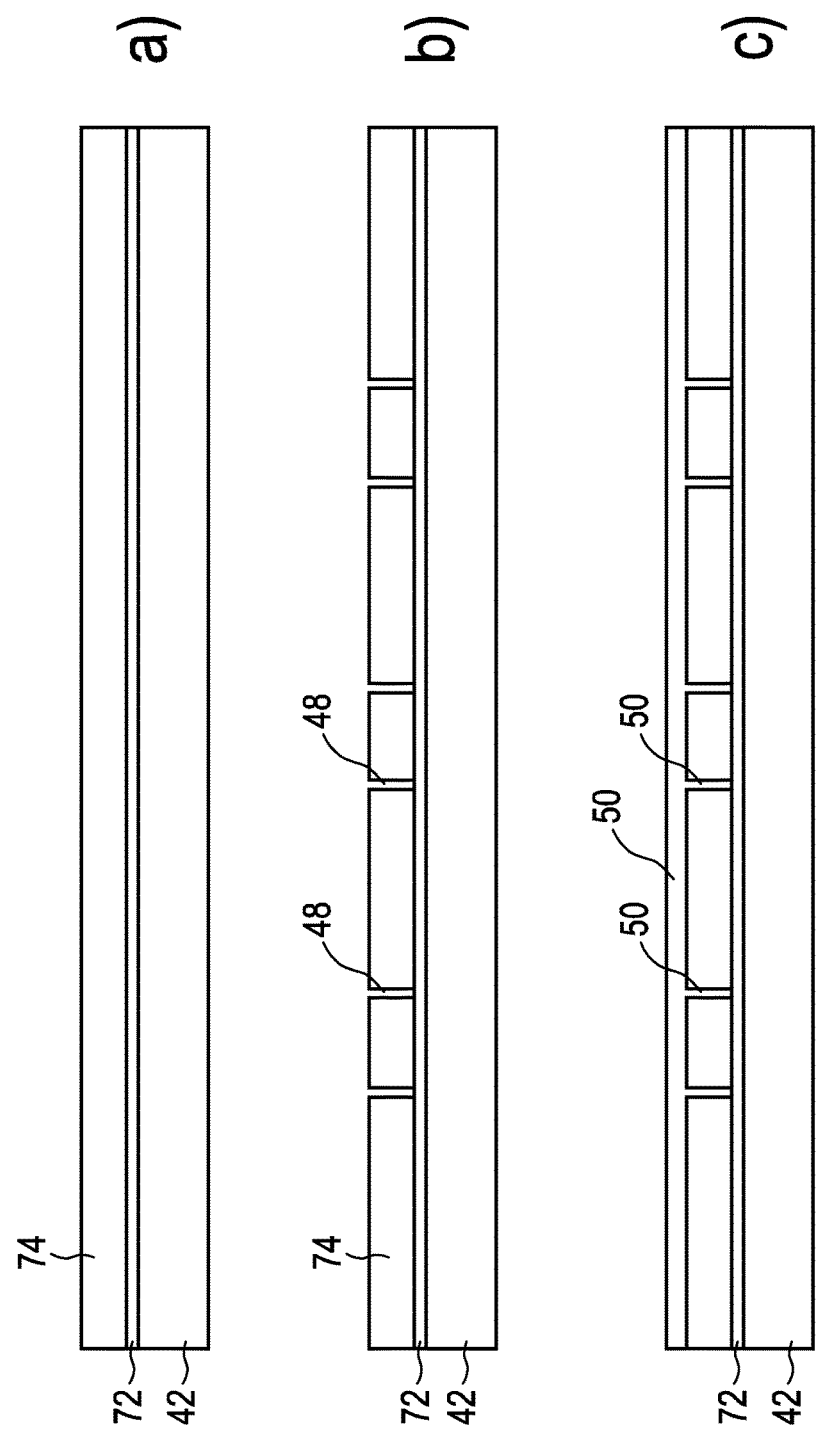

ULTRASOUND TRANSDUCER ASSEMBLY AND METHOD FOR MANUFACTURING AN ULTRASOUND TRANSDUCER ASSEMBLY

This application is the U.S. National Phase application under 35 U.S.C. § 371 of International Application No. PCT/EP2015/054301, filed on Mar. 2, 2015, which claims the benefit of European Application Serial No. 14159036.4, filed Mar. 12, 2014. These applications are hereby incorporated by reference herein.

FIELD OF THE INVENTION

The present invention relates to an ultrasound transducer assembly, in particular a capacitive micro-machined ultrasound transducer (CMUT) cell for intravascular ultrasound transducer and a method of manufacturing the same. The present invention relates further to ultrasound transducer.

BACKGROUND OF THE INVENTION

In the field of intravascular ultrasound devices, it is generally known to mount an ultrasound transducer on the tip of a catheter to form a radial ultrasound image e.g. of a blood vessel or the surrounding tissue. The ultrasound transducer elements may be rotated in order to emit and receive ultrasound waves in the radial direction of the catheter.

It is further known to replace the mechanically scanning ultrasound transducer elements in the intravascular ultrasound devices by electronically scanning devices having an annular array of ultrasound transducer elements, which are usually formed by piezoceramic transducers and which may be replaced in future applications by capacitive micro-machined ultrasound transducers (CMUT). These capacitive micro-machined ultrasound transducers are manufactured on the basis of a silicon wafer by means of IC process technologies and can be manufactured with low costs and can be scaled down to the dimensions of an intravascular ultrasound transducer.

For manufacturing an annular ultrasound transducer, a semi-flexible ultrasound transducer array is formed on the basis of a silicon wafer substrate that is optionally wrapped or bent around and attached to a cylindrically shaped submount structure in order to form the annular array and to transmit and receive ultrasound transducer waves in the radial direction of a catheter. These semi-flexible ultrasound transducer arrays consist usually of several silicon elements comprising ultrasound transducer elements which are connected to each other by a flexible element, so that the rigid silicon elements can be wrapped around a cylindrically shaped submount structure.

A bendable micro-machined ultrasound transducer array, which can be attached to a cylindrical submount structure to form the cylindrically-shaped ultrasound transducer array is known from US 2005/0146247 A2.

An electromechanical transducer including a multiple cellular structure is known from EP 2 441 530 A2, wherein a front silicon film is electrically connected to a rear surface of the multiple cellular structure by means of a via plug.

The silicon elements of the ultrasound transducer, which are flexibly connected have to be fabricated with high precision and the electrical functionality of the integrated ultrasound transducer elements and the electrical circuits have to be guaranteed in order to assure the functionality of the ultrasound transducer array in general.

SUMMARY OF THE INVENTION

It is an object of the present invention to provide an ultrasound transducer assembly, in particular for intravascular ultrasound systems, having an improved reliability and which can be manufactured precisely with low technical effort.

In a first aspect of the present invention, an ultrasound transducer assembly, in particular for intravascular ultrasound systems is provided, comprising:
  at least one silicon substrate element including an ultrasound transducer element for emitting and receiving ultrasound waves and including electrical connectors for electrically connecting the transducer element,
  wherein the substrate element has a top surface, a bottom surface and a side surface connecting the top surface and the bottom surface, and
  wherein an isolation layer is provided, which is formed at the side surface or which forms the side surface for electrically isolating the substrate element.

In a further aspect of the present invention, a method for manufacturing an ultrasound transducer assembly, in particular for intravascular ultrasound systems, is provided comprising the steps of:
  providing a silicon substrate having a substrate element portion including at least one ultrasound transducer element for transmitting and receiving ultrasound waves and including electrical connectors for electrically connecting the transducer element,
  forming a trench in the silicon substrate laterally separating the substrate element portion from an intermediate substrate portion surrounding the substrate element portion,
  filling the trench with a material different from the silicon substrate material to form a side layer of the substrate element portion, and
  removing the intermediate substrate portion surrounding the side layer to separate the substrate element portion from the silicon substrate.

In a still further aspect of the present invention, an ultrasound transducer, in particular for intravascular ultrasound systems is provided comprising an elongated probe including a tip and an ultrasound transducer assembly of this kind for emitting and receiving ultrasound waves.

Preferred embodiments of the invention are defined in the dependent claims. It shall be understood that the claimed method has similar and/or identical preferred embodiments as the claimed device and as defined in the dependent claims.

The present invention is based on the idea to manufacture the silicon substrate elements, which form a part of the bendable ultrasound transducer assembly in a micro-fabrication process on the basis of a silicon substrate which include the ultrasound transducer elements and electrical circuits for connecting the same. The side surface of the silicon substrate elements are isolated electrically by means of the isolation layer, which is formed at or forms the side surface of the substrate element in order to avoid short circuits. Hence, the silicon substrate elements have due to the electrical isolation less malfunctions so that the overall reliability of the ultrasound transducer assembly is improved. Further, the manufacturing method is based on the idea to first form trenches in the silicon substrate and to fill the trenches with a material different from the silicon substrate material to form the substrate elements in the respective substrate element portion and to remove the intermediate substrate in a following step to separate the substrate element from the silicon substrate. Since the trenches are formed laterally separating the substrate element portion from the intermediate substrate portion and the intermediate substrate portion is removed in a separate step to separate the substrate element from the silicon substrate, the trenches can be formed precisely by means of an accurate manufacturing step e.g. an anisotropic etch process like DRIE and the intermediate substrate portion can be removed by a coarse process step e.g. by an isotropic etch process like wet etching. Since the dimensions are defined by the trenches, which can be produced by a reduced technical effort and since the intermediate substrate portion is removed entirely by a coarse process step, the accuracy of the manufacturing process can be increased with low technical effort. The side surface, which is formed by the isolation layer forms an outer or exterior surface of the substrate element. The outer surface can be adjacent to a hole in the substrate element or can surround the substrate element. This is a possibility to isolate the substrate elements from other substrate elements or from a connection wire.

Consequently, the overall reliability of the ultrasound transducer assembly can be improved and the technical effort for a precise manufacturing of the ultrasound transducer assembly can be reduced.

In a preferred embodiment, the ultrasound transducer assembly comprises a plurality of silicon substrate elements separated from each other and a flexible connection layer for flexibly connecting the substrate elements to each other. This is a possibility to achieve a semi-flexible ultrasound transducer assembly which can be manufactured by means of an IC process technology and can be wrapped or bended around a submount structure in order to form an annular array of transducer elements.

In a preferred embodiment, a top isolation layer is formed at the top surface or forms the top surface for isolating the silicon substrate element. This is a possibility to further improve the electrical isolation of the silicon substrate element and to improve the overall reliability of the ultrasound transducer assembly.

In a preferred embodiment, a bottom isolation layer is formed at the bottom surface or forms the bottom surface for isolating the silicon substrate element. This is a possibility to improve the electrical isolation of the silicon substrate element in order to improve the overall reliability of the ultrasound transducer assembly.

In a preferred embodiment, an electrical connection pad is connected to the flexible connection layer for electrically connecting the transducer assembly to a catheter. This is a possibility to provide an electrical connection with low technical effort.

In a preferred embodiment, the isolation layer comprises silicon oxide or a polymer material. This is a possibility to provide an isolation layer which can be manufactured with low technical effort.

In a preferred embodiment of the method, a plurality of substrate element portions are laterally separated by a plurality of trenches, wherein the intermediate substrate portions between the substrate element portions are removed to separate the substrate element portions from the silicon substrate. This is a possibility to manufacture a plurality of substrate elements in parallel with the same manufacturing method in order to provide an ultrasound transducer assembly having a plurality of silicon substrate elements and a plurality of ultrasound transducer elements.

In a preferred embodiment, the trenches are formed vertically from a first side of the silicon substrate and the intermediate substrate portion is removed from a second side of the silicon substrate opposite to the first side of the silicon substrate. This is a possibility to utilize different manufacturing processes, which can be applied from different sides of the silicon substrate, wherein the trenches and the filled-in material predefine the shape of the substrate elements, which can be separated by a coarse manufacturing process from the opposite side of the substrate.

In a preferred embodiment, the intermediate substrate portion is removed by an etching process and the side layer forms a lateral etch stop layer for the etching process. This is a possibility to define the substrate element portion by means of a precise etching process for etching the trenches and to remove the intermediate substrate portion by a coarse etching process since the substrate element portions are protected by the etch stop layer.

In a preferred embodiment, a flexible layer is formed at a portion overlaying the intermediate substrate portion between the two substrate element portions to form a flexible connection between the substrate element portions. This is a possibility to flexibly connect the substrate elements after the substrate elements are separated from the silicon substrate by means of the flexible layer which is overlapping the intermediate substrate portion and connected to a surface of the substrate element portions to be connected.

In a preferred embodiment, the silicon substrate comprises a first and a second silicon layer disposed on top of each other separated by an intermediate layer, wherein the substrate element portion is formed in the first silicon layer and the intermediate layer forms a vertical etch stop layer. This is a possibility to precisely determine the thickness of the substrate elements since the thickness is determined by the position of the etch stop layer.

In a preferred embodiment, the intermediate layer is patterned by an etch mask and an etch process in order to expose the intermediate substrate portion surrounding the side layers. This is a possibility to remove the intermediate substrate portion between the side layer with low technical effort.

In a preferred embodiment, the trench is filled with an isolation material to form the side layer as an isolation layer. This is a possibility to manufacture the substrate elements having a high reliability, since the electrical functional is assured by the isolation of the side surface of the substrate elements.

As mentioned above, the ultrasound transducer assembly has an improved reliability, since the silicon substrate elements formed on the basis of a silicon substrate in an IC process are electrically isolated by the isolation layer formed at the side surface so that short circuits and the related malfunctions can be avoided. Further, since the trenches are formed in the silicon substrate to laterally separate the substrate element portions and filled with a material different from the silicon substrate material, the shape of the substrate elements can be precisely defined by the trench-etching process and the intermediate substrate portion can be easily removed by a coarse process e.g. an isotropic etch process so that the precise shape of the substrate elements can be achieved with low technical effort.

BRIEF DESCRIPTION OF THE DRAWINGS

These and other aspects of the invention will be apparent from and elucidated with reference to the embodiment(s) described hereinafter. In the following drawings

DETAILED DESCRIPTION OF THE INVENTION

Figure 1:
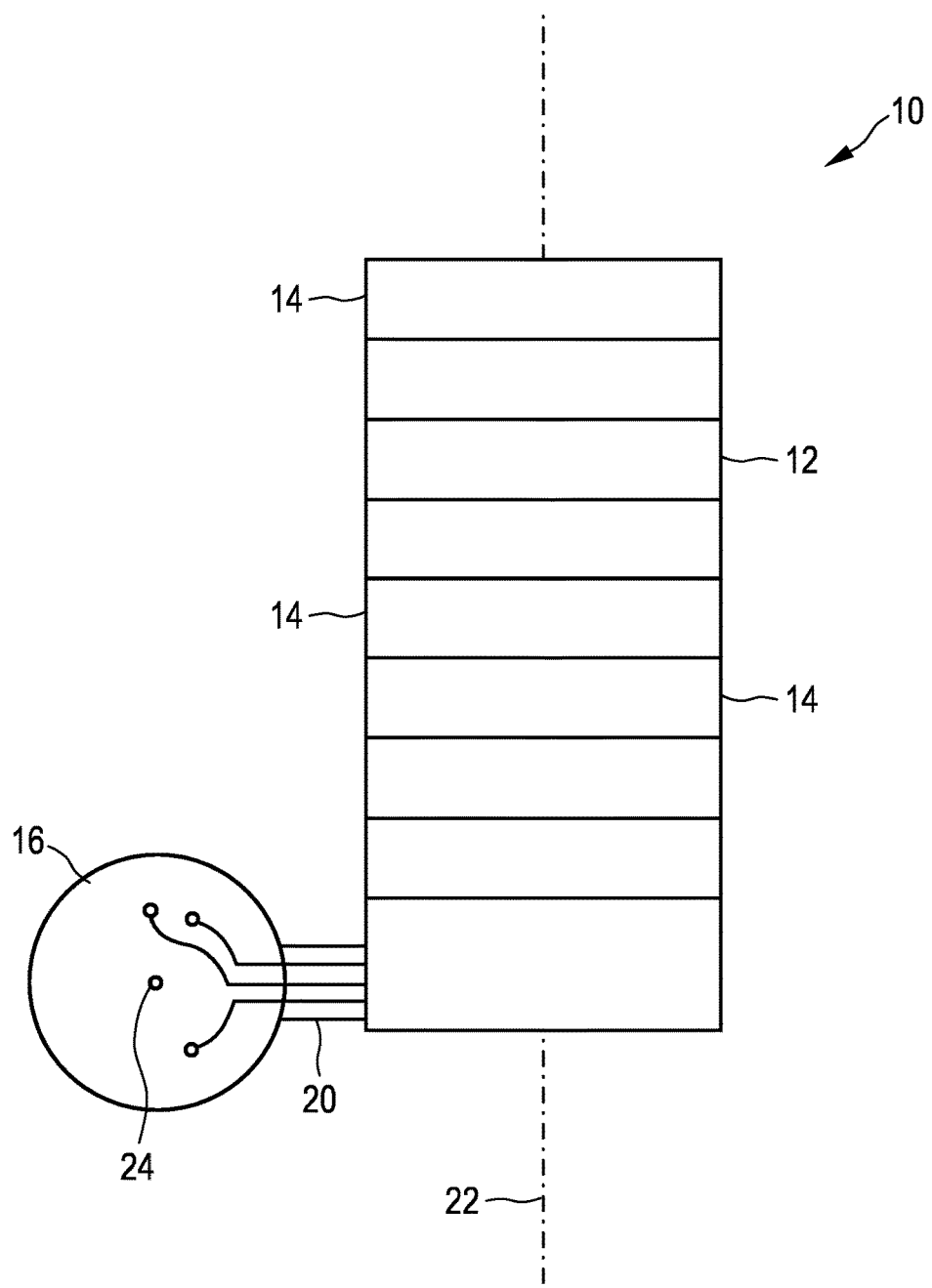
FIG. 1 shows a schematic drawing of an ultrasound transducer assembly in a plane view before assembling.

FIG. 1 shows a schematic top view of an ultrasound transducer assembly generally denoted by 10. The transducer assembly comprises a transducer array 12 including a plurality of transducer elements 14 for emitting and receiving ultrasound waves. The ultrasound transducer assembly 10 comprises a support element 16 which serve as a submount element for the transducer array 12. The support element 16 has a circular shape and is connected to the transducer array 12 by means of a flexible connection layer 20. The transducer array 12 has an elongated shape in the direction of a longitudinal axis 22.

The transducer elements 14 are formed as capacitive micro-machined ultrasound transducers (CMUT). The transducer elements are flexibly connected to each other so that the transducer array 12 can be bent in order to form an annular, circular or polygonal transducer array as described in the following. The transducer elements 14 can be flexibly connected to each other by means of a flexible layer, which may be connected in one piece to the connection layer 20.

The support element 16 comprises a central opening 24 in order to support the transducer assembly 10. The flexible connection layer 20 flexibly connecting the support element 16 to the transducer array 12 comprises integrated electrical interconnects for electrically connecting the transducer elements 14 to the support element 16.

The transducer assembly 10 is made from a silicon wafer by means of a micro-fabrication process using integrated circuit-processing technology to form the transducer array 12 and the support element 16 as described in the following. The silicon wafer may be a blank wafer or may include pre-processed active devices or circuits like CMOS transistors and or (high-density) capacitors. The transducer elements 14 may consist of silicon islands containing ultrasound transducer elements such as CMUT transducers, electrical circuits and or capacitors connected to each other by means of the flexible connection layer 20.

The support element 16 is connected to the transducer array 12 by means of the flexible connection layer 20 so that the support element 16 can be bent by 90° and the flexible transducer array can be wrapped around the support element 16 in order to form the transducer assembly 10 in a circular form. The so-formed transducer assembly 10 may be connected to an intravascular ultrasound system for emitting and receiving ultrasound waves in a radial direction.

The embodiment shown in FIG. 1 comprises a linear array of transducer elements 14, however any shape and any formation of transducer elements 14 is possible and can be used by the present invention, e.g. circular or polygonal transducer elements which are disposed in a one-dimensional array or a two-dimensional array including columns and rows of transducer elements 14 which may be alternatingly displaced.

Figure 2:
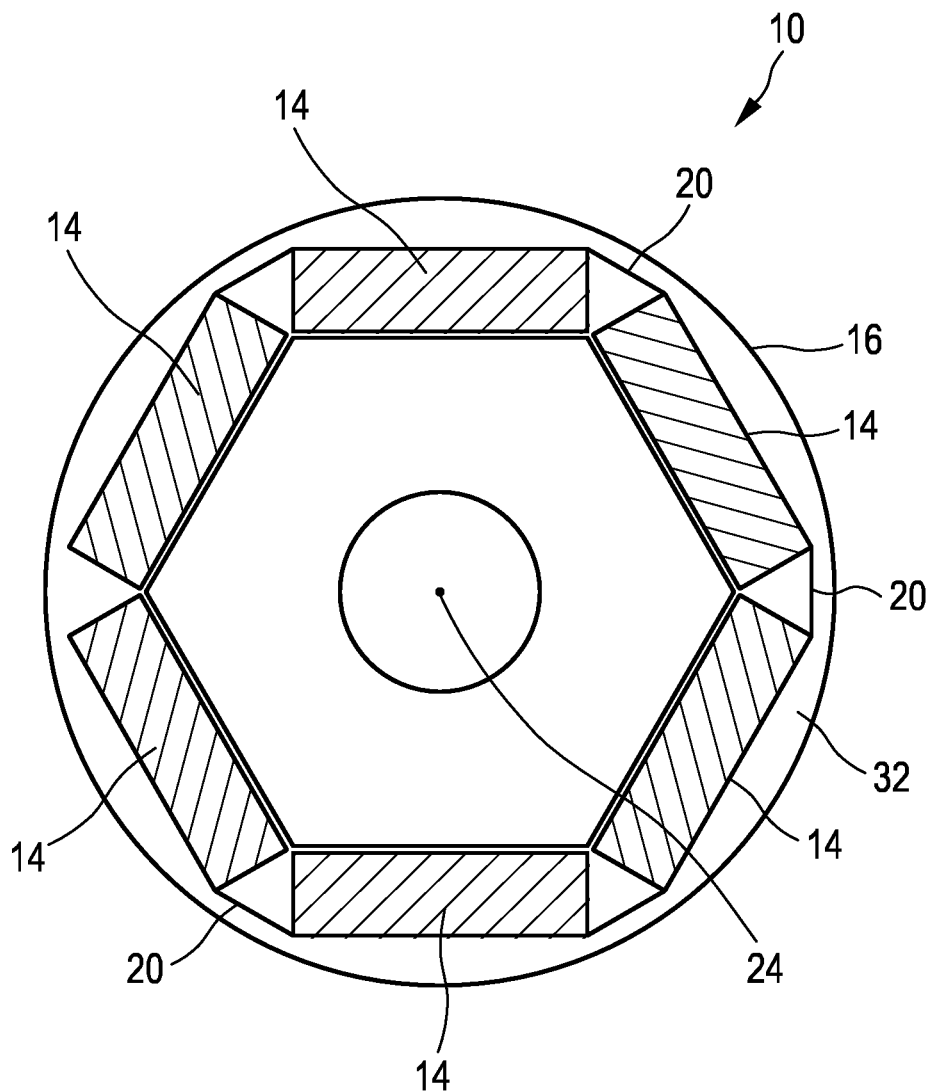
FIG. 2 shows a schematic drawing of a cross section of the assembled ultrasound transducer assembly in an axial view.

FIG. 2 shows a schematic cross-sectional view of the ultrasound transducer assembly 10 in an axial viewing direction. The transducer elements 14 are wrapped around the multi-phased support portion of the support element 16 and respectively attached to the different phases of the support portion. The transducer elements 14 are flexible connected to each other by means of the connection layer 20 which is provided at the outside of the transducer array 12. By means of the so-assembled transducer assembly 10 ultrasound waves can be transmitted and detected in a radial direction of the transducer assembly 10.

The size of the transducer elements 14, which are formed in a silicon substrate have a submillimeter size and require a precise shape and a correspondingly precise manufacturing process and an isolation from each other in order to provide a reliable functionality.

Figure 3:
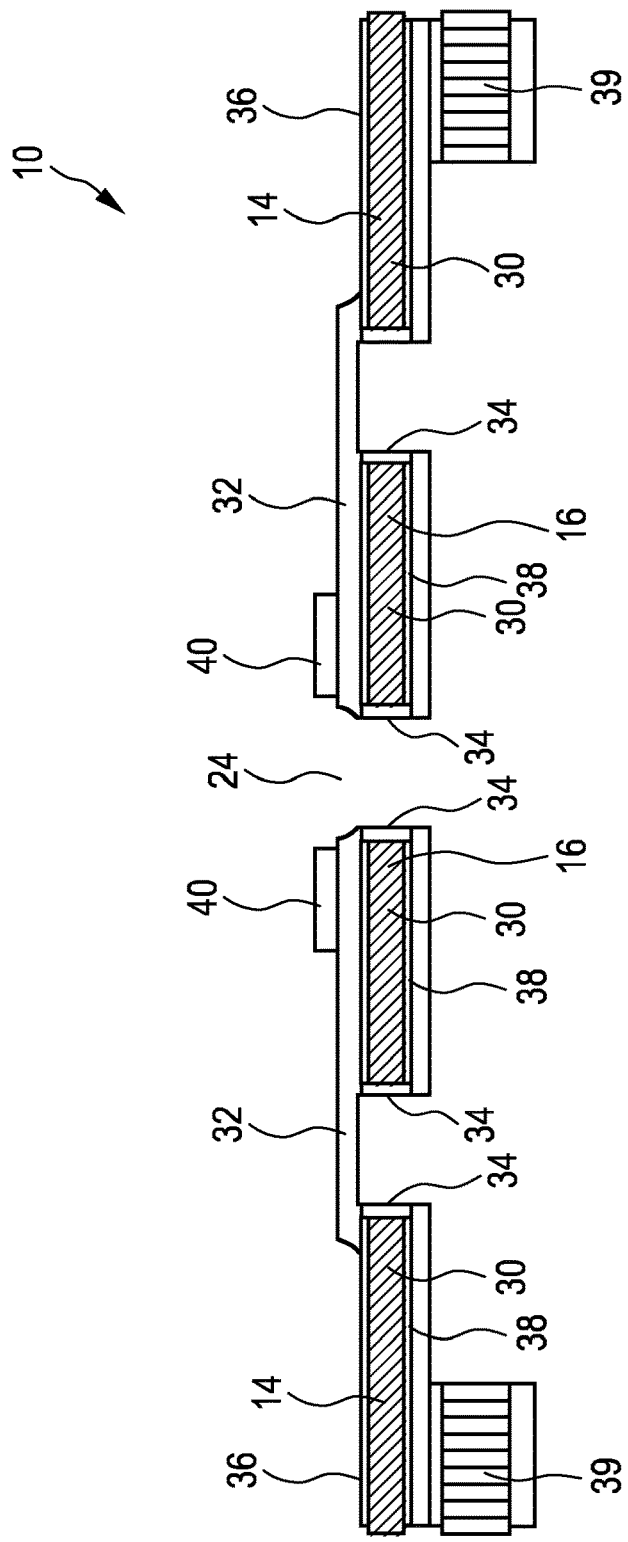
FIG. 3 shows a cross-sectional view of a processed silicon wafer including silicon substrate elements forming different ultrasound transducer elements of the ultrasound transducer assembly.
Figure 4:
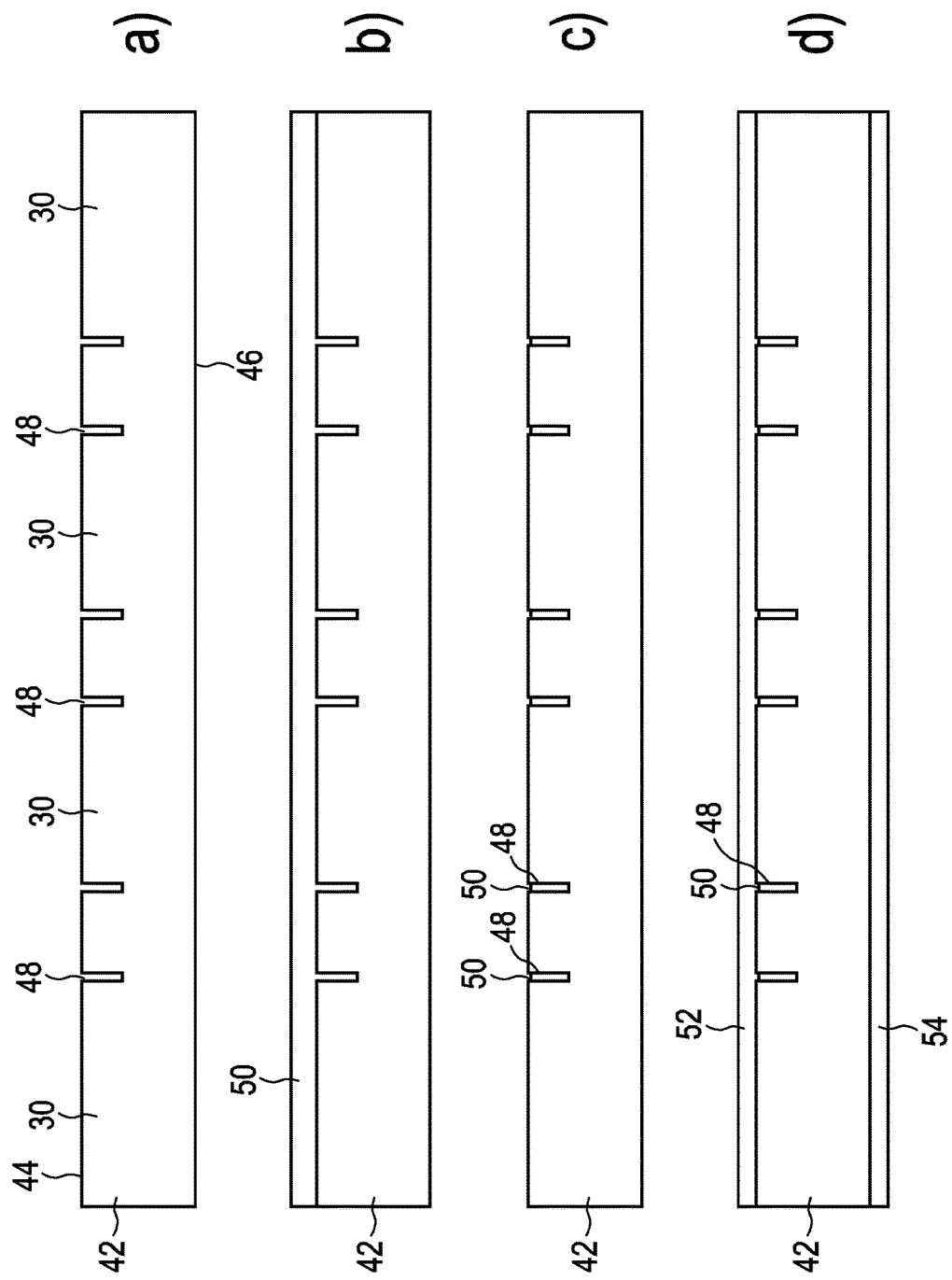
FIGS. 4a-l show a sequence of manufacturing steps for manufacturing the ultrasound transducer assembly.
Figure 4:
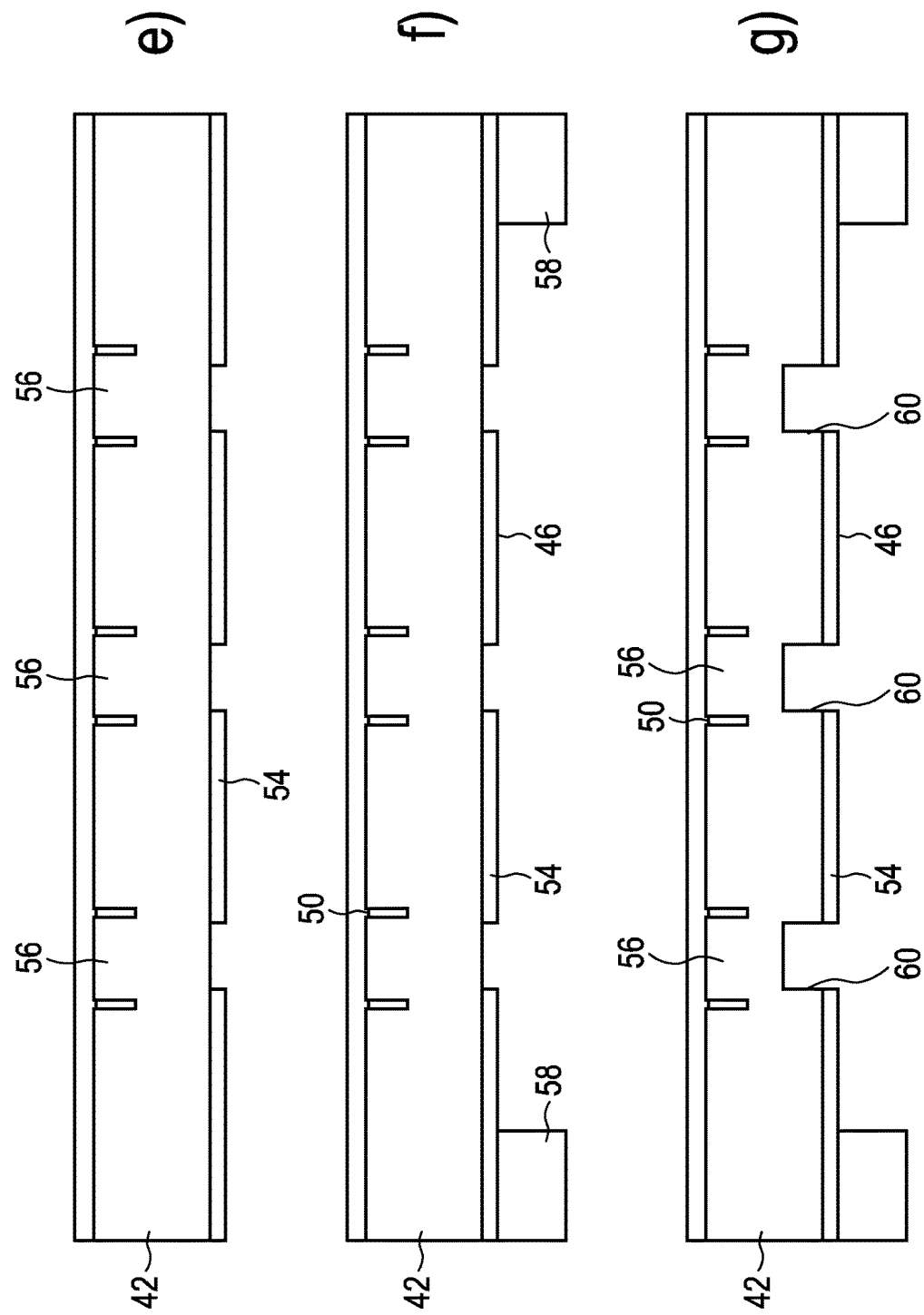
Figure 4:
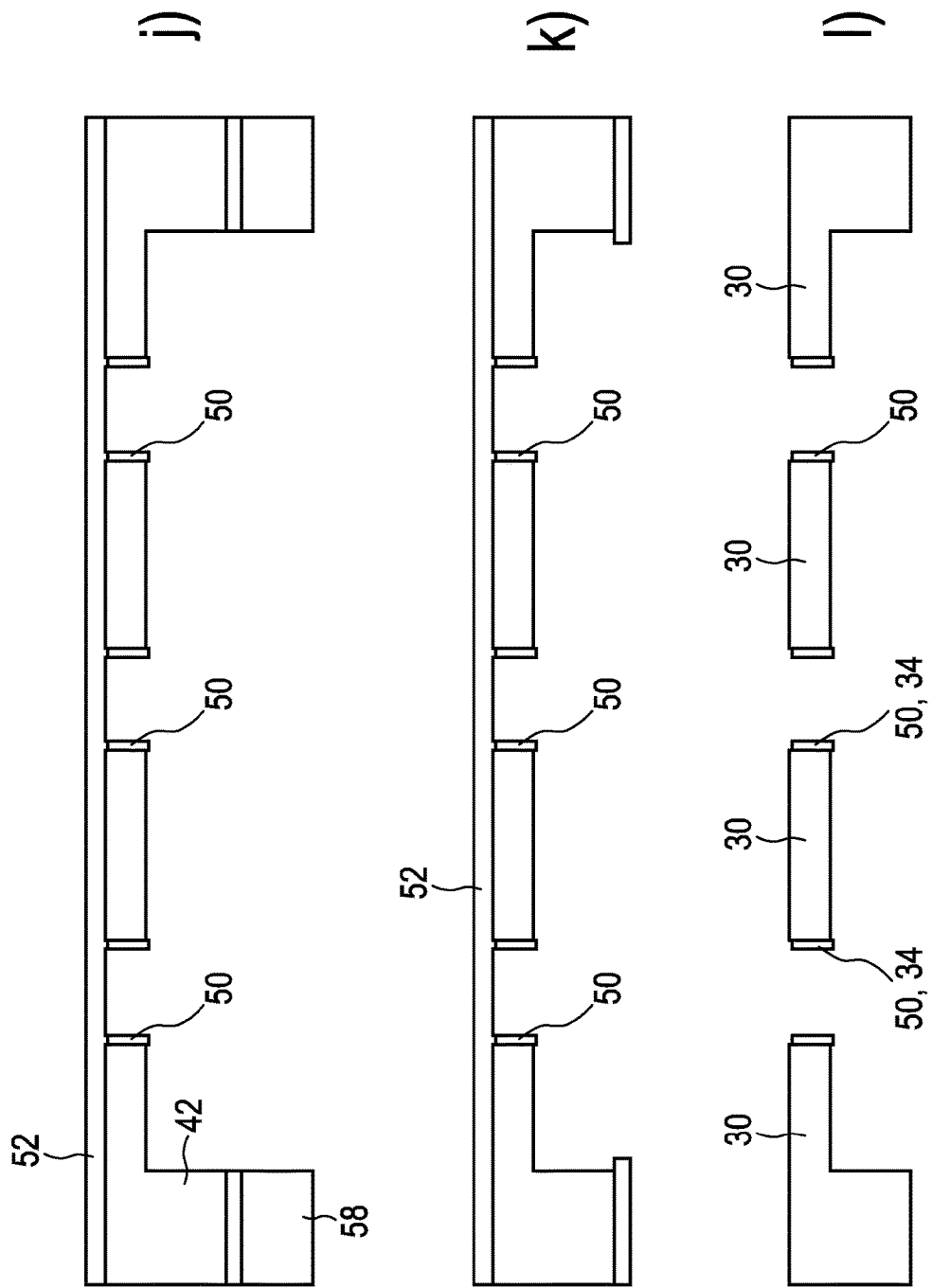

FIG. 3 shows a sectional view of an ultrasound transducer assembly 10 formed by an IC process in a silicon substrate. The transducer assembly 10 comprises different silicon substrate elements 30, which may form the transducer elements 14 including electrical circuits for electrically connecting the transducer elements 14. The substrate elements 30 are separated from each other and flexibly connected to each other by means of a flexible connection layer 32, which is preferably formed of a polyimide, a parylene or a PDMS layer. The substrate elements 30 are isolated by means of a side isolation layer 34 formed at a side surface of the substrate elements 30. The side isolation layer 34 form an outer side surface or an exterior surface of the substrate elements 30. In other words, the side isolation layer 34 is exposed to the outside or the exterior. The substrate elements 30 are further isolated by means of a top isolation layer 36 formed at a top surface and by means of a bottom isolation layer 38 formed at a bottom surface of the substrate elements 30. The outer substrate elements 30 are each attached to a lower support element 39, which are provided for supporting the substrate elements 30 radially after bending. On the top surface of the polyimide layer 32 connection pads 40 are connected for connecting the ultrasound transducer elements 14 to a catheter core wire.

The central substrate elements 30 may form the support element 16 having the central opening 24 to support the ultrasound assembly 10. The polyimide layer 32 serves to flexibly connecting the substrate elements 30 to each other so that the substrate elements 30 can be bent in order to form the cylindrical shape of the assembled ultrasound transducer assembly 10 as shown in FIG. 2.

The side isolation layer 34 serves in particular to isolate the substrate elements 30 electrically from each other so that short circuits can be avoided and the reliability of the ultrasound transducer assembly 10 can be improved. The side isolation layer 34 further serves as vertical etch stop layer in order to improve the preciseness of the manufacturing process as described in the following.

In FIG. 4a-l manufacturing steps for manufacturing an embodiment of the ultrasound transducer assembly 10 from a silicon substrate are shown.

In FIG. 4a a silicon substrate is shown having a thickness in the order of 500 μm as a basis for the manufacturing process. The silicon substrate is generally denoted by 42. The silicon substrate 42 comprises a front side 44 and a back side 46. In a first step, shown in FIG. 4*a*, vertical trenches 48 are formed from the front side 44 in the silicon substrate 42. The trenches 48 have a width in the order of 1-5 µm and a typical depth in the order 50 µm. The trenches 48 are formed by an anisotropic etch process e.g. a DRIE etch process. The trenches 48 laterally separate the substrate elements 30, which are formed by means of the manufacturing process.

In a following step shown in FIG. 4*b* an etch stop layer 50 is deposited on the front side 44 which fills the trenches 48. The etch stop layer may be formed by oxide, nitride or polymer like polyimide, benzo-cyclobutene and parylene.

In a following step (FIG. 4*c*), the etch stop layer 50 is etched back so that only the trenches 48 remain filled with the etch stop layer 50.

In the following step shown in FIG. 4*d* a etch-stop layer 52 is deposited on the front side 44 and a hard-mask layer 54 is deposited on the back side 46.

In the following steps shown in FIGS. 4*e-g* the hard mask 54 on the back side 46 is patterned at an intermediate substrate portion 56 between the trenches 48, the etch stop layers 50 and between the substrate elements 30. The intermediate substrate portions 56 have to be removed in order to separate the substrate elements 30 as described in the following. In a following step shown in FIG. 4*f*, a photoresist 58 is formed on the back side 46 and the back side 46 is etched so that trenches 60 are formed at a back side of the intermediate portions 56. In a following step, the hard mask 54 is removed from the back side 46 as shown in FIG. 4*h*. Hence, the back side 46 of the silicon substrate 42 is exposed including the trenches 60 at the position corresponding to the intermediate portions 56.

In a following etch process step, the back side 46 is etched in an anisotropic etch process so that the trenches 60 are etched down to the intermediate portions 56 as shown in FIG. 4*i*. In this state, a layer between the trenches 60 and the etch stop layers 50 is remaining having typically a thickness of 3-5 µm. At this point, the etching process is switched to an isotropic etching process. The silicon of the silicon substrate 42 will be etched in the vertical and in the lateral direction so that the remaining layer between the trenches 60 and etch stop layers 50 is entirely removed as shown in FIG. 4*j*. In this state, the intermediate portions 56 are entirely removed and the etch stop layers 50 are exposed laterally at one side. Due to the etch stop layer 50, the isotropic etch process does not affect the lateral side of the substrate elements 30, since the etch stop layer 50 protect the substrate elements 30 from being laterally etched. Hence, the precision of the trenches 48 formed by the anisotropic precise etching process for the front side 44 determine the lateral size of the substrate elements 30. Further, the back side 46 can be etched by a coarse isotropic etch process so that the technical effort for etching the back side 46 can be reduced.

In the following step, the etch-stop layer 52 and the hard mask 54 are removed so that the substrate elements 30 comprising the etch stop layer 50, which are identical to the side isolation layers 34 remain as shown in FIG. 4*l*.

Figure 5:
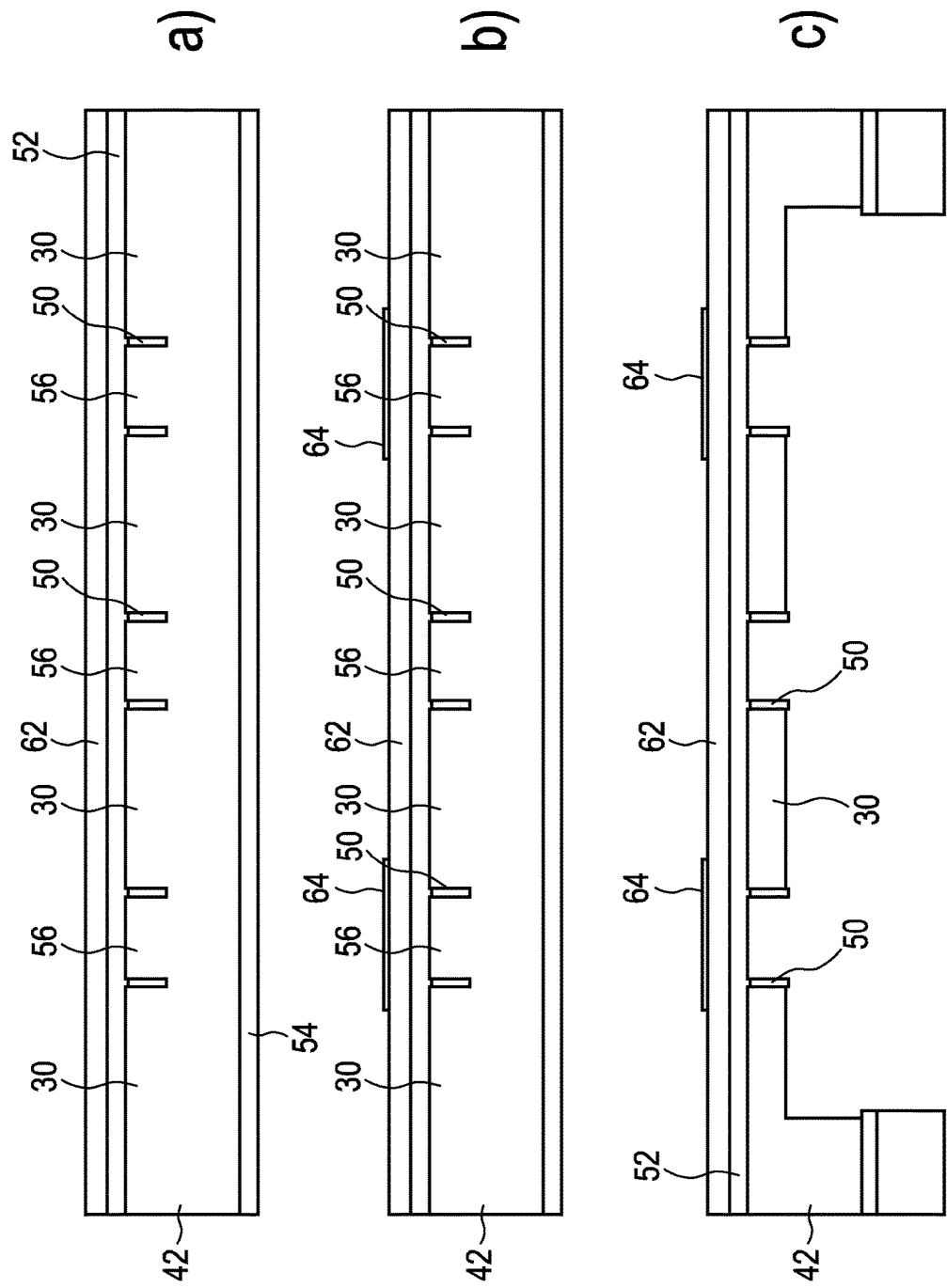
FIGS. 5a-e show an alternative sequence of manufacturing steps for manufacturing the ultrasound transducer assembly.
Figure 5:
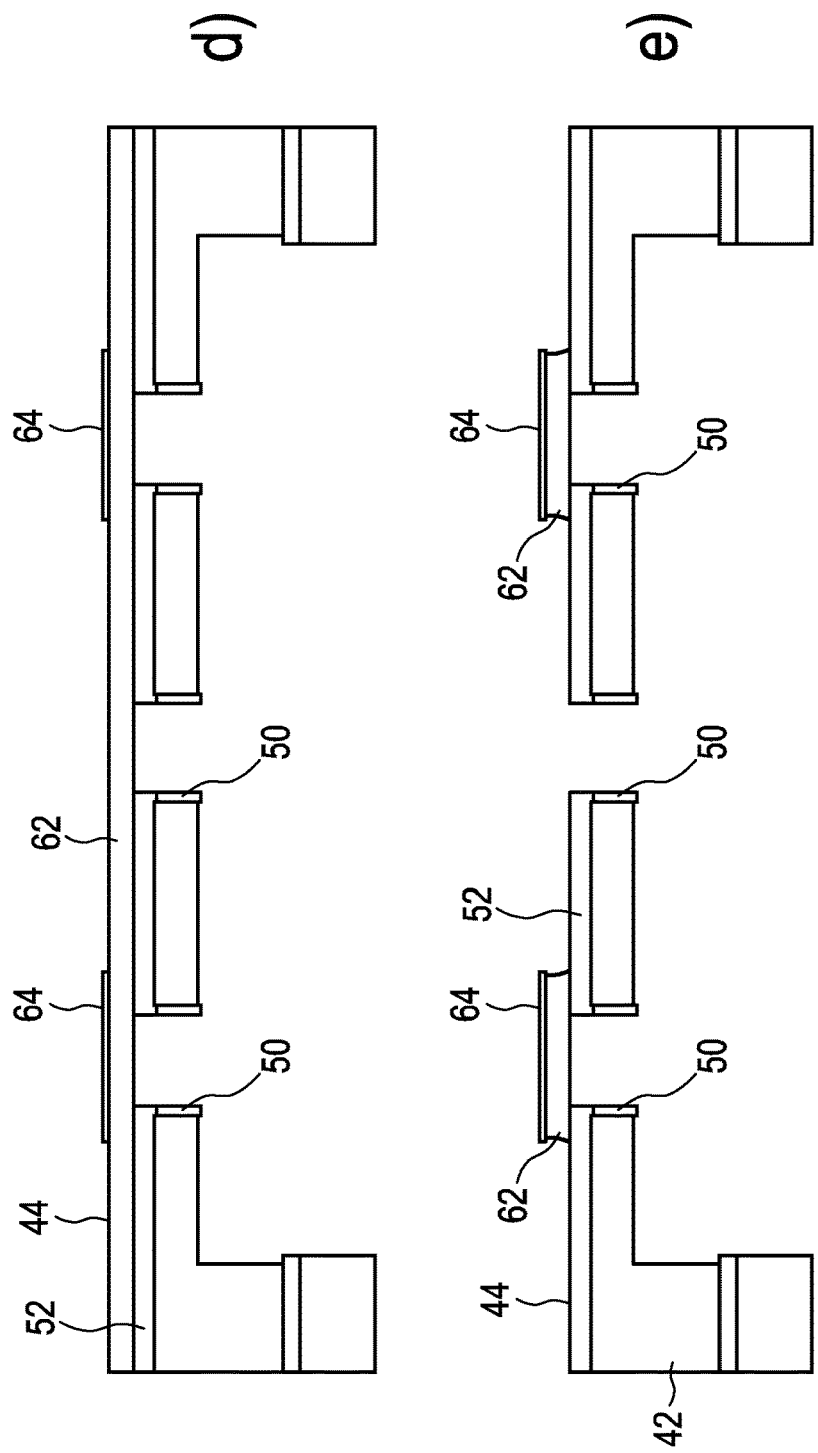

In FIG. 5*a-e* process steps are shown for manufacturing the ultrasound transducer assembly 10 including the flexible connection layer 32 for flexibly connecting the substrate elements 30 to each other. This process roughly follows the process shown in FIG. 4 after the etch stop layer 50 is formed at the front side 44 of the silicon substrate 42. Identical elements are denoted by identical reference numerals, wherein here merely the differences are explained in detail. In FIG. 5*a* a polyimide layer 62 is deposited onto the front side 44 and onto the etch stop layer 52. The polyimide layer 62 may be just a layer of plane polyimide or multiple layers containing interconnects which electrically connect the different substrate elements 30 to each other in order to provide an electrical connection to the transducer elements 14. The polyimide layer 62 may alternatively be formed of any other polymer like parylene, PDMS or the like.

Before the etching of the back side 46, aluminium hardmask layer 64 is deposited and patterned on the polyimide layer 62. The hard-mask layer 64 is formed over the intermediate portions 56 and is overlapping with the substrate elements 30 correspondingly and is overlapping with the respective etch stop layer 50 in order to form the flexible connection layer 32 between the substrate elements 30 as described in the following. After the deposition of the hard-mask layer 64, the back side is etched in order to remove the intermediate portions 56 as shown in FIG. 5*c*, wherein the etch stop layer 50 forms lateral etch stops for the etching process and determines the shape of the substrate elements 30 as described above.

In a following process step, the etch stop layer 52, which is preferably a silicon oxide layer is etched from the back side through the opening formed between the etch stop layers 50 as shown in FIG. 5*d*. Consequently, the substrate elements 30 are in this state merely connected to each other by means of the polyimide layer 62. In a final step, the polyimide layer 62 on the front side 44 is etched in an oxygen plasma using the aluminium hard-mask layer 64 on the front side 44 as a hard-etch mask so that the polyimide layer 62 merely remains below the hard-mask layer 64 and flexibly and, if applicable, electrically connects the respective substrate elements 30 as shown in FIG. 5*e*.

In FIGS. 6*a-h* process steps are shown for forming the electrical connection pads 40 on the front side 44 on top of the flexible layer 32. The process is comparable to the process shown in FIG. 5. Identical elements are denoted by identical reference numerals, wherein here merely the differences are explained in detail. The process starts after the deposition of the polyimide layer 62 shown in FIG. 6*a*, which is identical with FIG. 5*a*.

The electrical connection pads 40 may be deposited on the polyimide layer 62 around intermediate portions 66, which forms a hole 24 in the support element 16 in which a tip of a connection wire can be inserted. The electrical connection pads 40 are intended for electrical connection of the transducer elements 14. The connection pads 40 are formed around the hole 24, which is in this case formed as a central hole 24, however, the hole 24 may be formed at any position separate from the centre of the ultrasound assembly 10. Further, the ultrasound assembly 10 may comprise a plurality of connection pads 40 formed at different positions and/or around different holes in order to form an electrical connection. The central hole 24 may have other functions than an electrical connection, e.g. forming a mechanical support portion.

Figure 6:
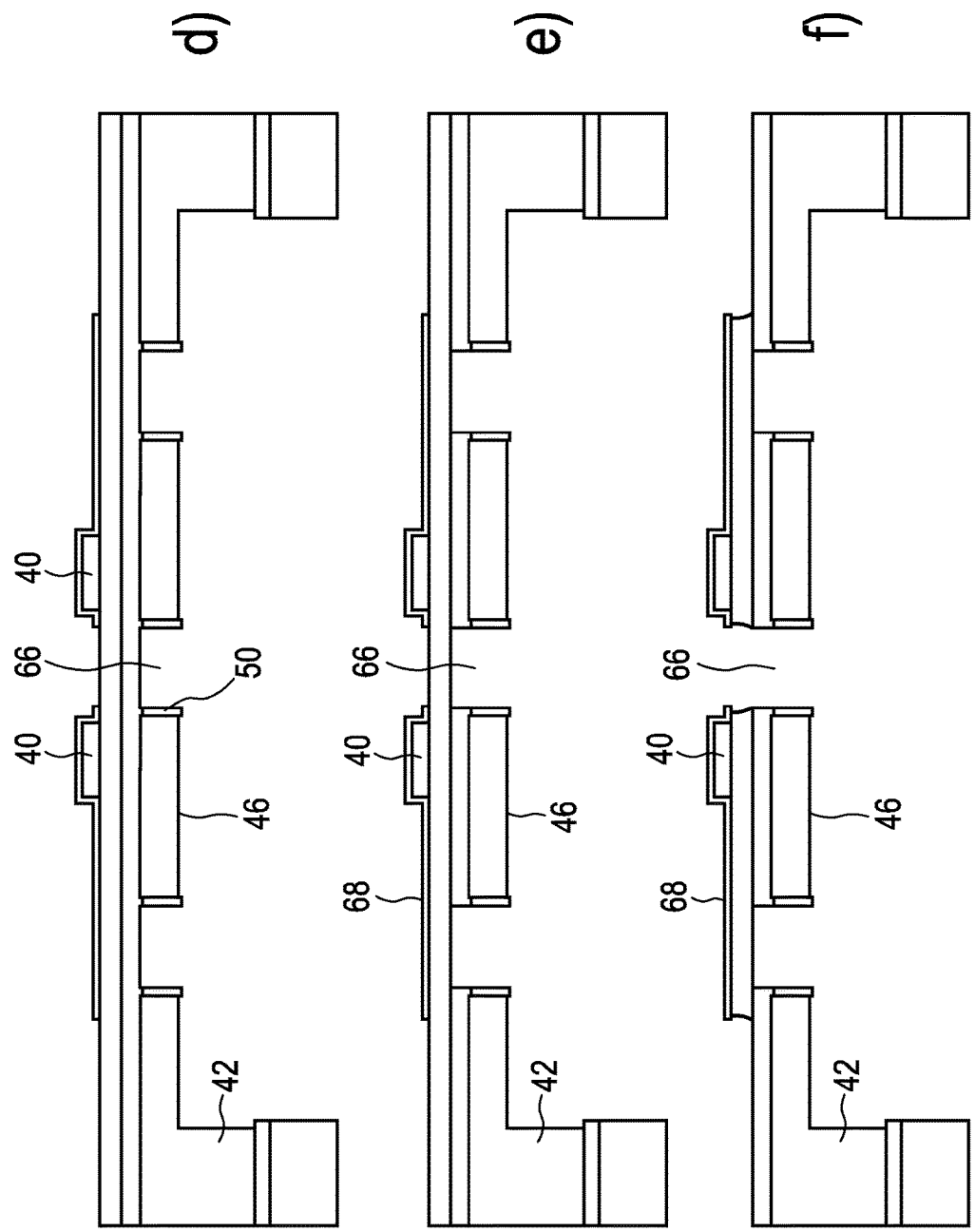
FIGS. 6a-h show an alternative sequence of manufacturing steps for manufacturing the ultrasound transducer assembly.
Figure 6:
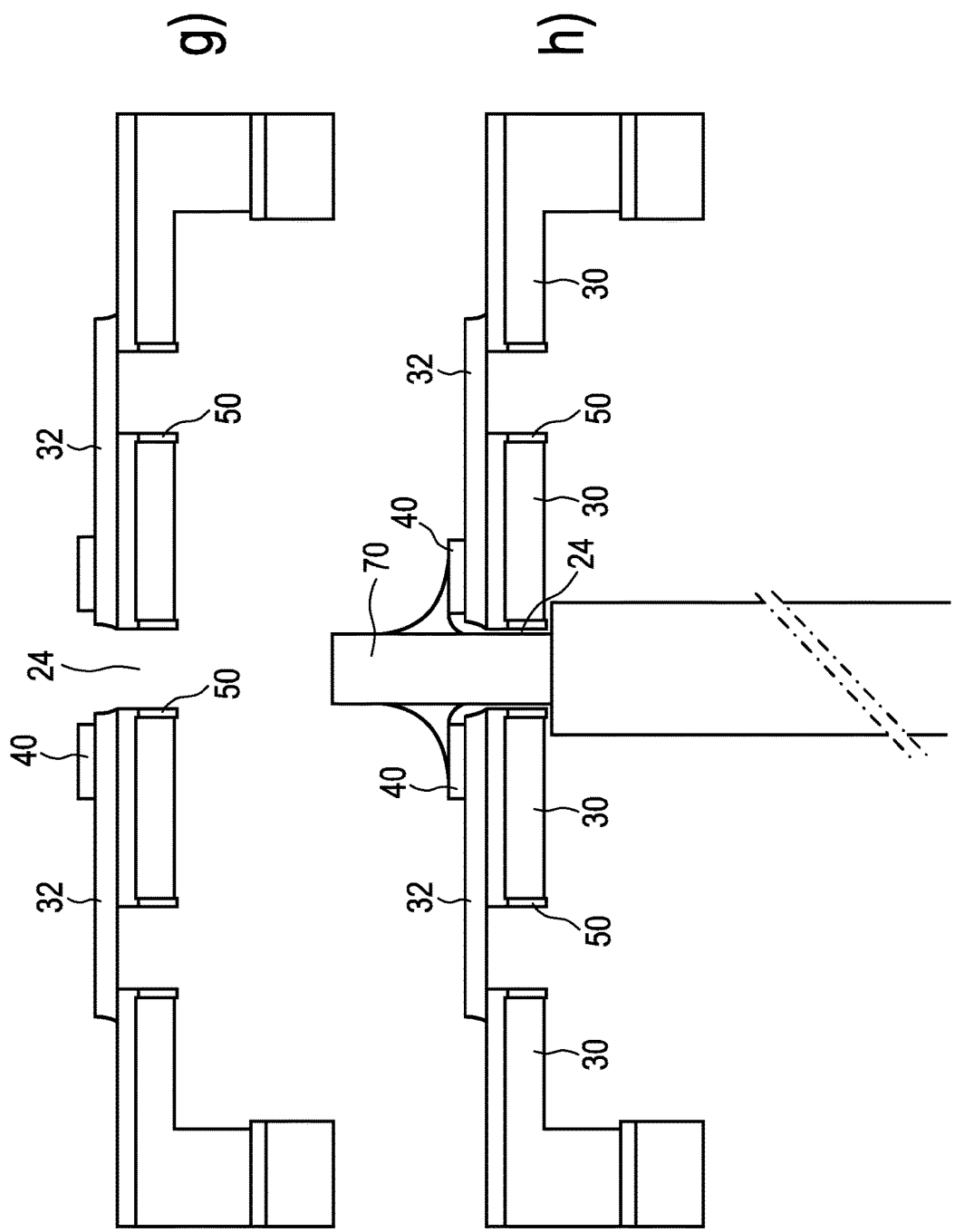

In a following step a hard-mask layer 68 is deposited and patterned onto the connection pads 40 and is formed preferably of aluminium as shown in FIG. 6*c*.

In the following steps shown in FIGS. 6*d* and *e*, the substrate 42 and the etch stop layer 52 are etched from the back side 46 as described before.

In a following step, the polyimide layer 62 is etched by means of the oxygen plasma from the front side so that the polyimide layer 62 which is not covered by the hard mask 68 is removed as shown in FIG. 6*f*.

In a following step shown in FIG. 6*g*, the aluminium layer as the hard-mask 68 is removed so that the substrate elements 30 are connected to each other by means of the flexible layer 32 and the connection pads 40 are connected to the flexible connection layer 32.

A connection wire 70 may be inserted into the opening 24 and soldered to the connection pads 40 in order to form an electrical connection to the substrate element and to support the transducer elements 14. The substrate elements 30 on the outer side can be bent by means of the flexible connection layer 32 so that a cylindrical shape can be formed around the wire 70.

In FIGS. 7a-s manufacturing steps are shown for manufacturing the ultrasound transducer assembly 10, wherein the thickness of the substrate elements 30 is precisely determined with low technical effort.

In FIG. 7a, the substrate 42 is provided, wherein on the front side 44 an isolation layer 72 and a silicon layer 74 are formed. Hence, the substrate comprises the top silicon layer 74, the isolation layer 72 and the bottom silicon layer, which is corresponding to the silicon substrate 42. In the following steps shown in FIG. 7b-d, the etch stop layer 50 are formed by etching and filling the trenches 48 in the top silicon layer 74 as described above. In this step, the isolation layer 72 forms as an etch stop layer for the vertical etching of the trenches 48.

In a following step, the hard-mask layer 54 is formed at the back side 46 and a spin coating and curing of a polyimide layer 76 is performed on the front side 44 in order to form a 10 μm layer of polyimide 76.

In the following step, the connection pads 40 are formed around the intermediate portion 66, where the opening 24 of the support element 16 will be formed. The connection pads may be formed as a ring around the intermediate portion 66 e.g. by means of a sputter process and a patterning, wherein the connection pads 40 are preferably formed of a 1 μ, thick layer of aluminium. Before etching the back side 46, the aluminium hard-mask layer 68 is deposited and patterned on the front side 44 as described above.

In a following step, the hard mask 54 is patterned at the intermediate portions 56 so that the silicon substrate 42 is exposed at the intermediate portions 56.

In the following steps shown in FIGS. 7i and j, the photoresist 58 is formed at the back side 46 and the trenches 60 are etched in the silicon substrate 42 as described above.

In a following step shown in FIGS. 7k and l, the hard mask 54 is removed from the back side 46 and the silicon substrate 42 is etched in an anisotropic etch process preferably a DRIE etch process so that the trenches 60 are extended to the isolation layer 72 as shown in FIG. 7l.

Figure 7:
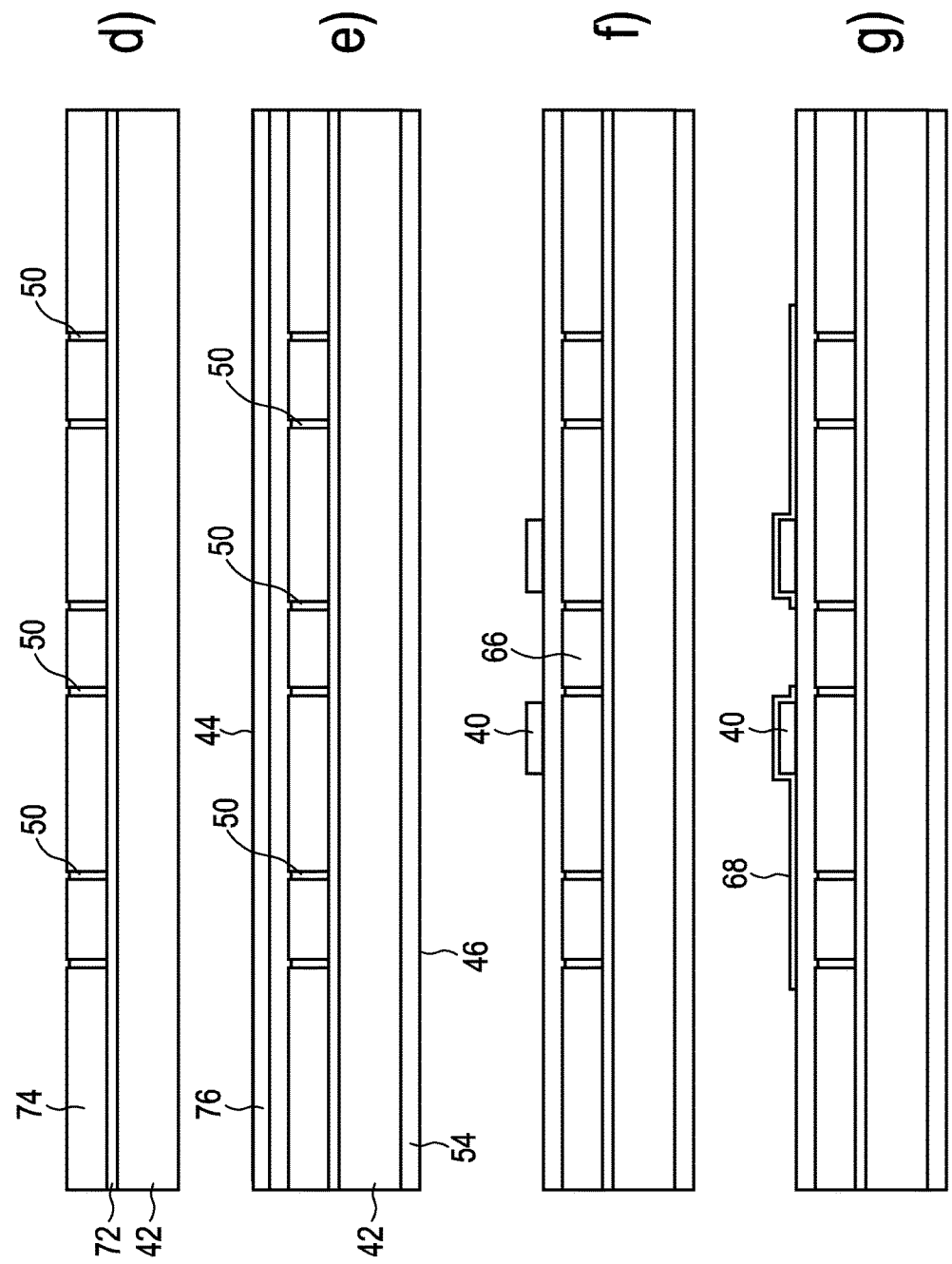
FIGS. 7a-s show a sequence of manufacturing steps for manufacturing the ultrasound transducer assembly including a horizontal etch stop layer.
Figure 7:
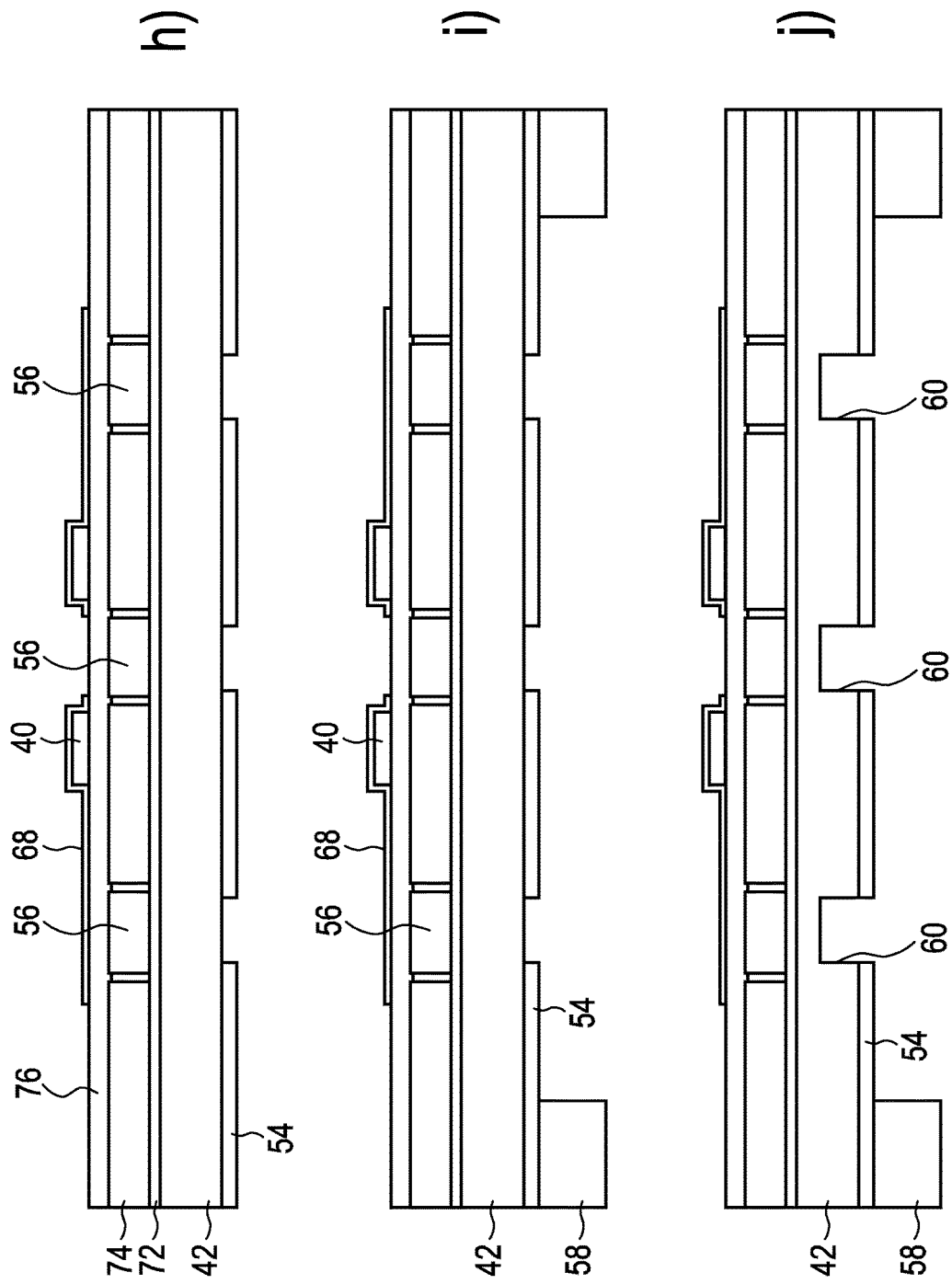
Figure 7:
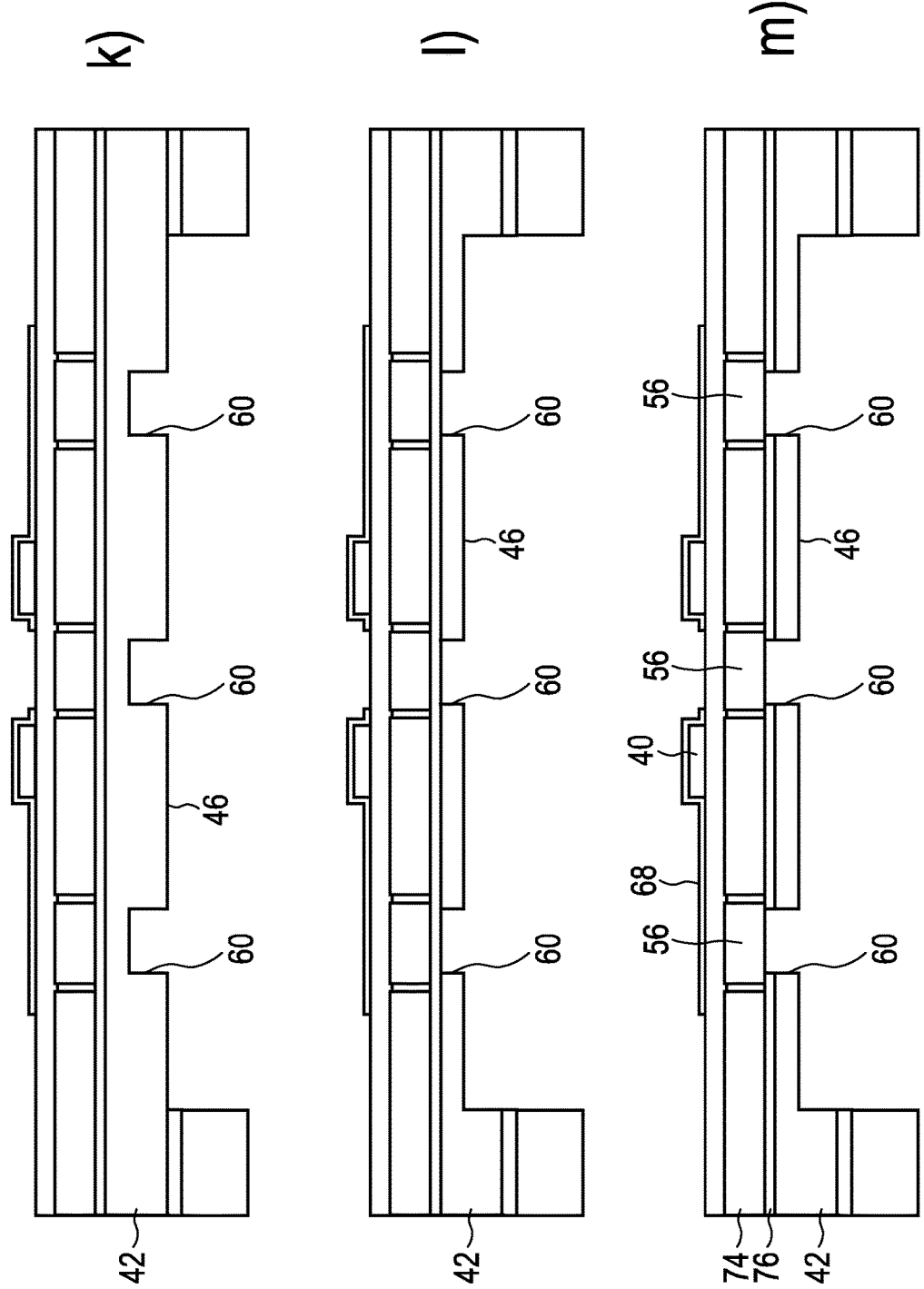
Figure 7:
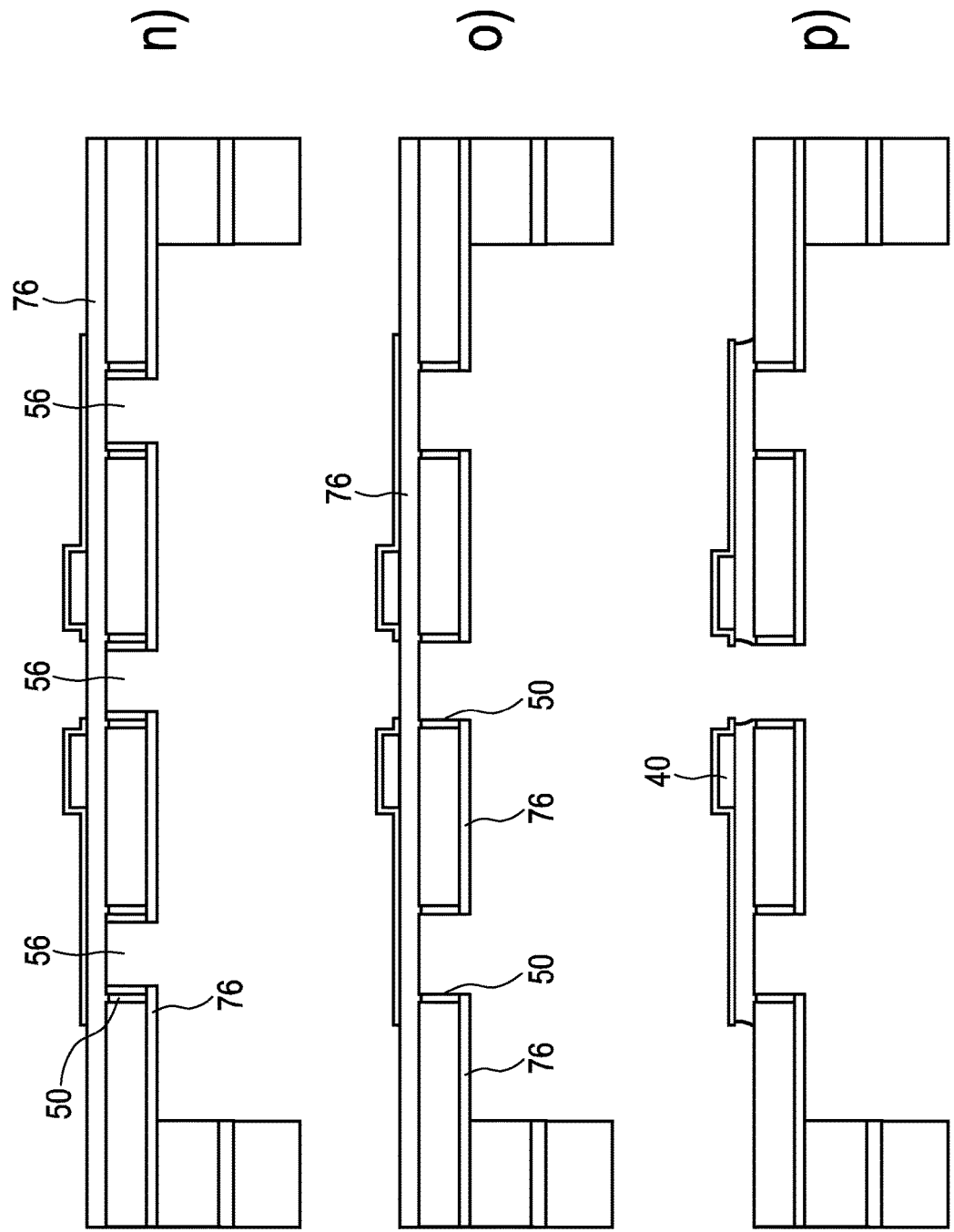
Figure 7:
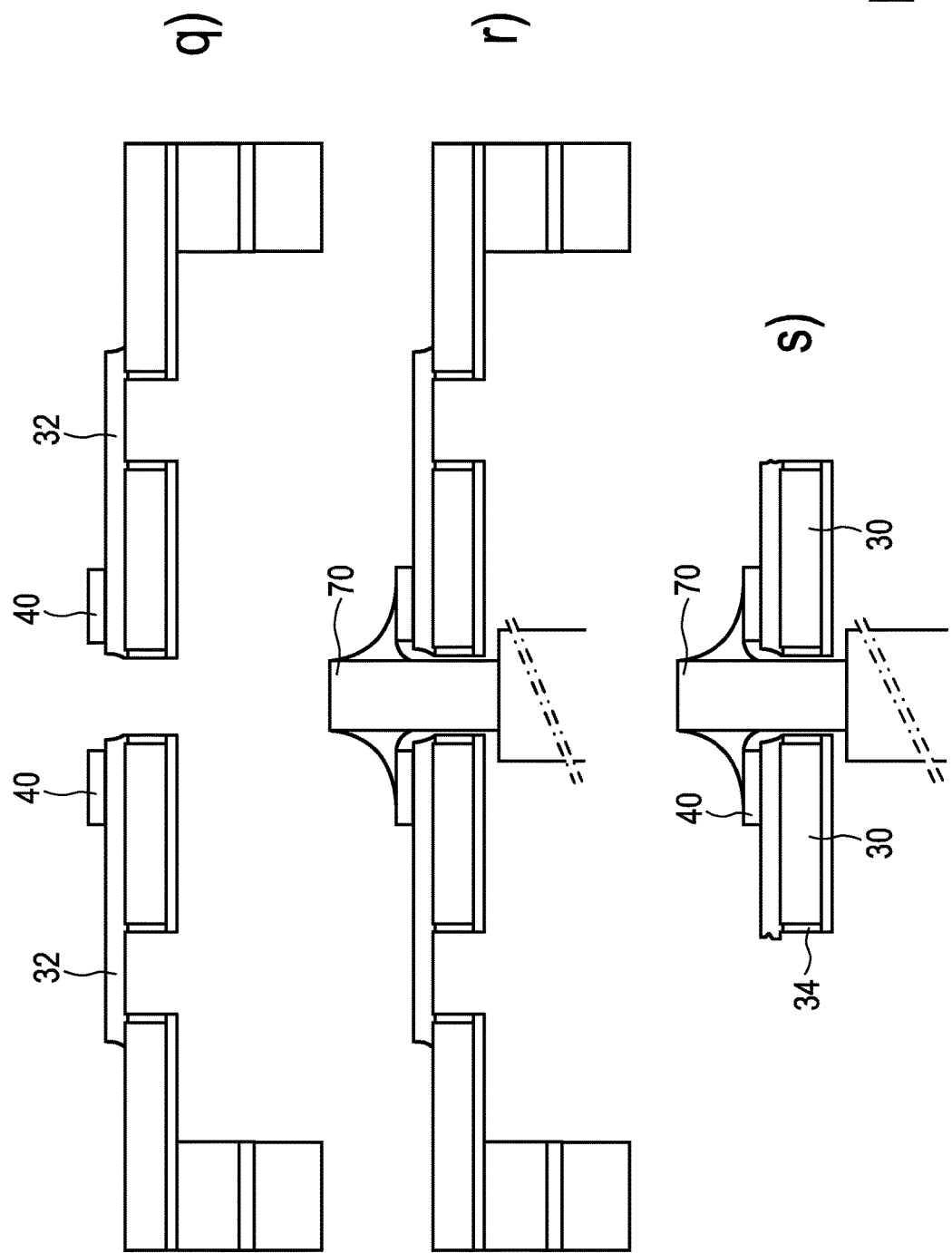

In a following step shown in FIG. 7, the isolation layer 72 is etched at the exposed positions corresponding to the trenches 60, wherein the remaining silicon substrate beside the trenches 60 is used as a mask layer.

In a following step shown in FIG. 7n, the remaining silicon of the intermediate portion 56 is etched by an DRIE etch process so that a layer of silicon is remained on the etch stop layers 50 as explained above.

The etching of the back side 46 is completed by an isotropic etch to remove the remaining silicon as describe above and as shown in FIG. 7o. The laterally etch stop is provided by the etch stop layer 50 and the isolation layer 72 forms and etch stop layer in the vertical direction so that the thickness of the substrate elements 30 is determined by the isolation layer 72.

In the following steps the polyimide layer 76 is etched by means of an oxygen plasma as shown in FIG. 7p and the aluminium hard-mask layer 68 is removed in the step shown in FIG. 7q. Hence, the substrate elements 30 are separated from each other and flexibly connected by means of the flexible connection layer 32 and connected to the connection pad 40, which may be formed as a ring around the hole 24. In FIG. 7r, the wire 70 is connected to the connection pads 40 in order to form an electrical connection to the ultrasound transducer elements 14 and/or in order to form a mechanical connection to the transducer elements 14.

Finally, the substrate elements 30 at the two sides may be bended to the wire 70 in order to form the cylindrical shape of the transducer assembly 10. Alternatively, the substrate elements 30 around the central hole which are connected to the wire 70 may be separated from the remaining substrate elements 30 by breaking the flexible layer 32 as shown in FIG. 7s.

Finally, the etch stop layer 50 forms the side isolation layer 34 and the isolation layer 72 which forms during the process the vertical etch stop layer forms the bottom isolation layer 38 and the polyimide layer 76 or an additional isolation layer forms the top isolation layer 36.

Hence, the ultrasound transducer assembly can be manufactured precisely with a precise shape of the substrate elements 30 with low technical effort and the substrate elements 30 can be isolated from each other by low technical effort so that the reliability of the ultrasound transducer assembly 10 is improved.

While the invention has been illustrated and described in detail in the drawings and foregoing description, such illustration and description are to be considered illustrative or exemplary and not restrictive; the invention is not limited to the disclosed embodiments.

Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality. A single element or other unit may fulfill the functions of several items recited in the claims. The mere fact that certain measures are recited in mutually different dependent claims does not indicate that a combination of these measures cannot be used to advantage.

The invention claimed is:

1. An ultrasound transducer assembly for intravascular ultrasound systems, comprising:
   a silicon substrate element including an ultrasound transducer element for emitting and receiving ultrasound waves and including electrical connectors for electrically connecting the ultrasound transducer element,
   wherein the silicon substrate element has a top surface, a bottom surface and a side surface connecting the top surface and the bottom surface to each other, and
   wherein an isolation layer forms the side surface connecting the top surface and the bottom surface to each other for electrically isolating the silicon substrate element, the isolation layer forming an exterior surface of the side surface of the silicon substrate element.

2. An ultrasound transducer assembly as claimed in claim 1, comprising a plurality of silicon substrate elements separated from each other and a flexible connection layer for flexibly connecting the substrate elements to each other.

3. An ultrasound transducer assembly as claimed in claim 1, wherein a top isolation layer is formed at the top surface for isolating the silicon substrate element.

4. An ultrasound transducer assembly as claimed in claim 1, wherein a bottom isolation layer is formed at the bottom surface for isolating the silicon substrate element.

5. An ultrasound transducer assembly as claimed in claim 2, wherein an electrical connection pad is connected to the flexible connection layer for electrically connecting the transducer assembly.

6. An ultrasound transducer assembly as claimed in claim 1, wherein the isolation layer comprises silicon oxide or a polymer material.

7. A method for manufacturing an ultrasound transducer assembly for intravascular ultrasound systems, comprising the steps of:
providing a silicon substrate having a substrate element portion including at least one ultrasound transducer element for transmitting and receiving ultrasound waves and including electrical connectors for electrically connecting the transducer element,
forming a trench in the silicon substrate laterally separating the substrate element portion from an intermediate substrate portion surrounding the substrate element portion,
filling the trench with an isolating material different from the silicon substrate material to form a side layer connecting a top layer and a bottom layer of the substrate element portion to each other, and
removing the intermediate substrate portion surrounding the side layer to separate the substrate element portion from the silicon substrate so that the isolating material electrically isolates the substrate elements from each other.

8. A method as claimed in claim 7, wherein a plurality of substrate element portions are laterally separated by a plurality of trenches and wherein the intermediate substrate portions between the substrate element portions are removed to separate the substrate element portions from the silicon substrate.

9. A method as claimed in claim 7, wherein the trenches are formed vertically from a first side of the silicon substrate and the intermediate substrate portion is removed from a second side of the silicon substrate opposite to the first side of the silicon substrate.

10. A method as claimed in claim 7, wherein the intermediate substrate portion is removed by an etching process and the side layer forms a lateral etch stop layer for the etching process.

11. A method as claimed in claim 7, wherein a flexible layer is formed at a portion overlaying the intermediate substrate portion between the two substrate element portions to form a flexible connection between the substrate element portions.

12. A method as claimed in claim 7, wherein the silicon substrate comprises a first and a second silicon layer disposed on top of each other separated by an intermediate layer, wherein the substrate element portion is formed in the first silicon layer and the intermediate layer forms a vertical etch stop layer.

13. A method as claimed in claim 7, wherein the intermediate layer is patterned by an etch mask and an etch process in order to expose the intermediate substrate portion surrounding the side layers.

14. A method as claimed in claim 7, wherein the trench is filled with an isolation material to form the side layer as an isolation layer.

15. An ultrasound transducer for vascular ultrasound systems, comprising an elongated probe including a tip and an ultrasound transducer assembly as claimed in claim 1 for emitting and receiving ultrasound waves.

16. The ultrasound transducer assembly as claimed in claim 2, wherein a central silicon substrate element of the plurality of silicon substrate elements form at least a portion of a support element.

17. The ultrasound transducer assembly as claimed in claim 2, wherein an outer silicon substrate element of the plurality of silicone substrate elements is coupled to a lower support element, wherein an upper surface of the lower support element is coupled to a lower surface of the outer silicon substrate element.

* * * * *